US012582738B1

(12) United States Patent
Guo

(10) Patent No.: US 12,582,738 B1
(45) Date of Patent: Mar. 24, 2026

(54) AROMATHERAPY DIFFUSER

(71) Applicant: Shenzhen Youda Technology Co., Ltd,
Shenzhen City (CN)

(72) Inventor: Weibin Guo, Shenzhen City (CN)

(73) Assignee: Shenzhen Youda Technology Co., Ltd,
Shenzhen City (CN)

( * ) Notice: Subject to any disclaimer, the term of this
patent is extended or adjusted under 35
U.S.C. 154(b) by 0 days.

(21) Appl. No.: 19/199,957

(22) Filed: May 6, 2025

(30) Foreign Application Priority Data

Apr. 18, 2025 (CN) ........................ 202520754994.X

(51) Int. Cl.
*A61L 9/14* (2006.01)
*A61M 21/02* (2006.01)
(52) U.S. Cl.
CPC .............. *A61L 9/14* (2013.01); *A61M 21/02*
(2013.01); *A61L 2209/11* (2013.01); *A61L*
*2209/133* (2013.01); *A61L 2209/134* (2013.01)
(58) Field of Classification Search
CPC .. A61L 9/14; A61L 2209/11; A61L 2209/133;
A61L 2209/134; A61M 21/02
See application file for complete search history.

(56) References Cited

U.S. PATENT DOCUMENTS

| | | | | |
|---|---|---|---|---|
| 9,211,357 | B1 * | 12/2015 | Li | ............................. A61L 9/00 |
| 10,967,092 | B2 * | 4/2021 | Chang | .................... A61L 9/013 |
| 11,097,032 | B2 | 8/2021 | Gao | |
| 11,197,941 | B1 | 12/2021 | Gao | |
| 2023/0355825 | A1 | 11/2023 | Long | |
| 2024/0207479 | A1 | 6/2024 | Long | |
| 2024/0335582 | A1 | 10/2024 | Ma | |

FOREIGN PATENT DOCUMENTS

CN            209680405 U      11/2019

* cited by examiner

*Primary Examiner* — Qingzhang Zhou
*Assistant Examiner* — Joel Zhou

(57) ABSTRACT

Disclosed is an aromatherapy diffuser, which is used to
mount an essential oil bottle to spray atomized essential oil
and includes: a main body provided with a first mist hole; an
atomization component arranged in the main body, wherein
the essential oil bottle is detachably mounted on the atomi-
zation component; and a flow guiding member arranged
between a first mist hole and the atomization component and
including a first flow guiding channel and a second flow
guiding channel mutually communicated, wherein the first
flow guiding channel is arranged in an arc shape, a hori-
zontal section of an inner side wall of the first flow guiding
channel is higher than a liquid level in the essential oil bottle.
The technical solution of the present invention effectively
improves the anti-leakage performance, thereby improving
the practicability of the aromatherapy diffuser.

15 Claims, 6 Drawing Sheets

AROMATHERAPY DIFFUSER

CROSS-REFERENCE TO RELATED APPLICATIONS

The application claims priority of Chinese patent application CN202520754994.X, filed on Apr. 18, 2025, which is incorporated herein by reference in its entireties.

TECHNICAL FIELD

The present invention relates to the technical field of aromatherapy equipment, and particularly to an aromatherapy diffuser.

BACKGROUND

With the popularization of aromatherapy equipment, essential oil bottles, as the core carrier of atomized essential oils, have use convenience and anti-leakage performance, which have become important indicators affecting user experience. Traditional essential oil bottles typically feature a straight-through first mist hole design. Specifically, a first mist hole is directly communicated with a liquid storage cavity inside the bottle body, and the essential oil is atomized and sprayed out via an airflow generated by an atomizer. However, this design has a significant defect: when the essential oil bottle is tilted, inverted, or accidentally knocked over during transportation or use, the liquid essential oil in the bottle easily overflows directly along the first mist hole under the action of gravity. This not only causes a waste of essential oils, but also pollutes the internal circuit components in a device and the surrounding desktop environment. Long-term residual essential oils may also corrode the housing of the device and affect the service life.

In view of this, how to construct a stable gas-liquid isolation barrier has become a technical problem that needs to be overcome urgently in this field.

SUMMARY

A primary objective of the present invention is to provide an aromatherapy diffuser, which aims to improve the anti-leakage performance and practicality of the aromatherapy diffuser.

To achieve the foregoing objective, the aromatherapy diffuser provided by the present invention is used to mount an essential oil bottle to spray atomized essential oil, and includes:

a main body provided with a first mist hole;

an atomization component, wherein the essential oil bottle is detachably mounted on the atomization component, and the atomization component is arranged in the main body; and a flow guiding member, wherein the flow guiding member is arranged between a first mist hole and the atomization component, the flow guiding member includes a first flow guiding channel and a second flow guiding channel mutually communicated, the first flow guiding channel is arranged in an arc shape, a horizontal section of an inner side wall of the first flow guiding channel is higher than a liquid level in the essential oil bottle, one end of the first flow guiding channel far away from the second flow guiding channel is provided with a mist inlet connected to the atomization component, and one end of the second flow guiding channel far away from the first flow guiding channel is provided with a mist outlet connected to the first mist hole.

Optionally, the first flow guiding channel is arranged in an annular shape, and the mist outlet is arranged close to a central axis of the flow guiding member relative to the mist inlet.

Optionally, the mist outlet is positioned at a central position of the flow guiding member.

Optionally, the mist inlet and the mist outlet are arranged in opposite directions along an axial direction of the flow guiding member.

Optionally, the first mist hole is opened on a top surface of the main body.

Optionally, the main body includes a mounting housing and a cover body detachably connected to the mounting housing, the atomization component is mounted on the cover body, the first mist hole is opened at a top of the cover body, and the essential oil bottle is positioned in the mounting housing.

Optionally, the cover body is provided with a rectifying cavity, the flow guiding member is arranged in the rectifying cavity, and the atomization component and the mist inlet are both communicated with the rectifying cavity.

Optionally, a fixing column protrudes from a peripheral side of the first mist hole in the rectifying cavity, and the mist outlet of the flow guiding member is sleeved on the fixing column.

Optionally, the atomization component includes a first mounting bracket, an atomizer fixedly mounted on the first mounting bracket, and an air pump arranged in the mounting housing, one end of the atomizer is communicated with a liquid in the essential oil bottle via a conduit, and another end of the atomizer is communicated with the air pump;

the cover body is provided with a mounting groove, the first mounting bracket is fixedly arranged in the mounting groove, the rectifying cavity is formed between the first mounting bracket and an inner wall of the mounting groove, and the first mounting bracket is provided with a second mist hole communicated with the rectifying cavity and the essential oil bottle.

Optionally, the atomization component further includes a second mounting bracket arranged in the mounting housing, the second mounting bracket is provided with an accommodating groove for accommodating the essential oil bottle, the first mounting bracket and the second mounting bracket are mutually buckled to form a sealed cavity, the air pump is arranged on the second mounting bracket and communicated with the sealed cavity, the first mounting bracket is provided with an airflow channel, one end of the airflow channel is communicated with the atomizer, and another end of the airflow channel is communicated with the sealed cavity.

Optionally, a check valve is also arranged in the airflow channel.

Optionally, an anti-overflow ball valve is arranged on one side of the second mist hole facing the essential oil bottle.

Optionally, the atomization component further includes a flow divider, and the flow divider is arranged in the rectifying cavity and corresponds to the second mist hole.

Optionally, the aromatherapy diffuser further includes a control component, the control component includes a main control board and a battery electrically connected to the main control board, and the main control board is electrically connected to the air pump.

Optionally, the flow guiding member is an integrally formed structure.

According to the technical solution of the present invention, the aromatherapy diffuser includes a main body, an atomization component arranged in the main body and a flow guiding member connected to the atomization component and a first mist hole, wherein the atomization component is used to detachably mount an essential oil bottle and atomize essential oil, the flow guiding member includes a first flow guiding channel and a second flow guiding channel mutually communicated, the first flow guiding channel is arranged in an arc shape, a horizontal section of an inner side wall of the first flow guiding channel is higher than a liquid level in the essential oil bottle, one end of the first flow guiding channel far away from the second flow guiding channel is provided with a mist inlet connected to the atomization component, and one end of the second flow guiding channel far away from the first flow guiding channel is provided with a mist outlet connected to the first mist hole. According to the foregoing structural design, when the aromatherapy diffuser is tilted, inverted or impacted, the arc-shaped arrangement of the first flow guiding channel may ensure that the inner side wall of the flow guiding member is always higher than the liquid level in the essential oil bottle, thereby preventing the essential oil from overflowing along the flow guiding member, and effectively preventing diffuser damage and environmental pollution caused by essential oil leakage. Therefore, the anti-leakage performance and the practicability of the aromatherapy diffuser are effectively improved.

BRIEF DESCRIPTION OF DRAWINGS

To more clearly illustrate the technical solutions in the embodiments of the present invention or in the prior art, the drawings required to be used in the description of the embodiments or the prior art are briefly introduced below. It is obvious that the drawings in the description below are only some embodiments of the present invention, and those of ordinary skill in the art can obtain other drawings according to structures illustrated in these drawings without creative efforts.

DESCRIPTIONS OF REFERENCE NUMERALS

Figure 1:
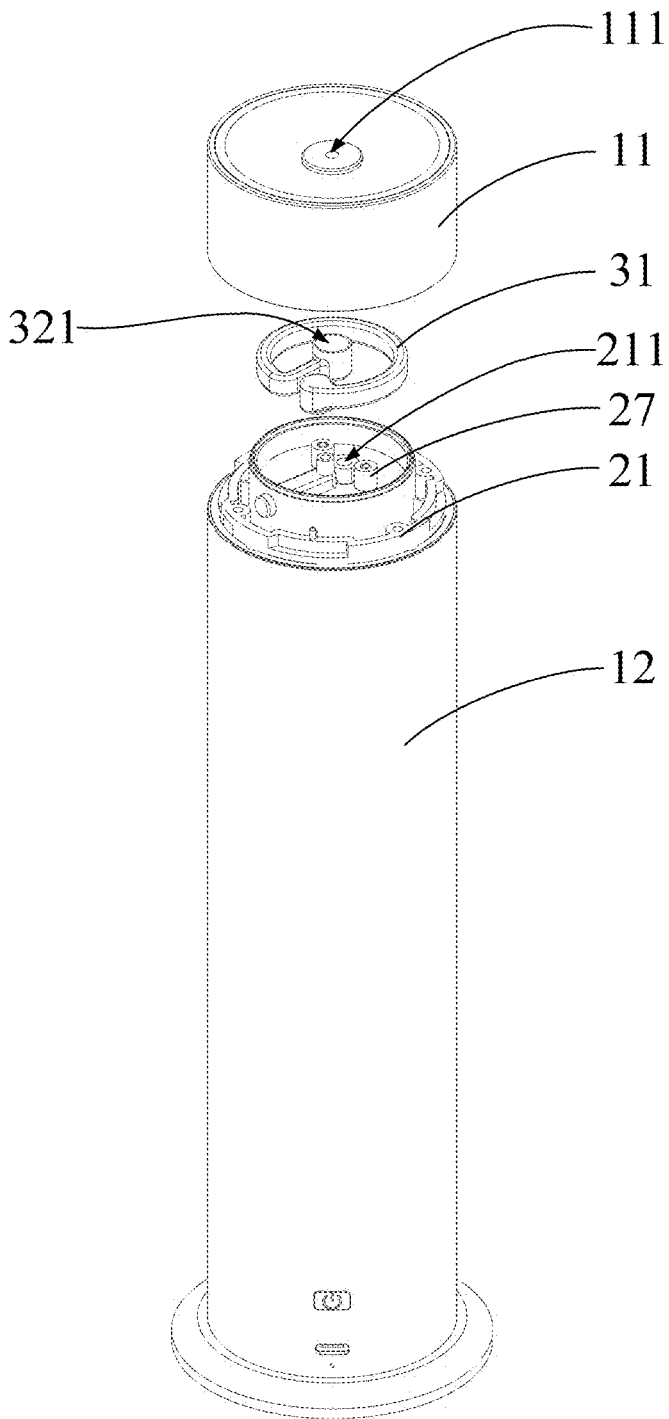
FIG. 1 is a schematic diagram of an exploded structure of an aromatherapy diffuser according to an embodiment of the present invention.

11: cover body; 111: first mist hole; 112: rectifying cavity; 113: fixing column; 114: mounting groove; 12: mounting housing; 21: first mounting bracket; 211: second mist hole; 212: airflow channels; 22: atomizer; 221: first channel; 222: second channel; 23: air pump; 24: second mounting bracket; 241: accommodating groove; 25: sealed cavity; 27: flow divider; 30: flow guiding member; 31: first flow guiding channel; 311: mist inlet; 32: second flow guiding channel; 321: mist outlet; 33: upper housing; 34: lower housing; 35: partition; 40: essential oil bottle; 41: conduit; 50: check valve; 60: anti-overflow ball valve; 71: main control board; and 72: battery.

The realization of the objectives, the functional features, and the advantages of the present invention will be further explained in conjunction with the embodiments and with reference to the drawings.

DETAILED DESCRIPTION OF EMBODIMENTS

The technical solutions in the embodiments of the present invention will be clearly and completely described below with reference to the drawings in the embodiments of the present invention. It is apparent that the described embodiments are only some, but not all, embodiments of the present invention. Based on the embodiments of the present invention, all other embodiments obtained by those of ordinary skill in the art without creative efforts fall within the protection scope of the present invention.

It should be noted that, if directional indications (such as upper, lower, left, right, front and rear) are involved in the embodiments of the present invention, the directional indications are only used to explain the relative positional relationships, the motion situations and the like between individual components under a certain pose (as shown in the drawings), and if the certain pose is changed, the directional indications are changed accordingly.

In addition, if there are descriptions relating to "first", "second" and the like in the embodiments of the present invention, the descriptions of "first", "second" and the like are for descriptive purposes only and are not to be construed as indicating or implying relative importance thereof or implicitly indicating the quantities of the indicated technical features. Thus, a feature defined by "first" or "second" may explicitly or implicitly include at least one such feature. In addition, "and/or" appearing herein is meant to include three parallel solutions, and taking "A and/or B" as an example, it includes solution A, or solution B, or both solution A and solution B. In addition, the technical solutions among various embodiments may be combined with each other, however, this combination must be based on that it can be realized by those of ordinary skill in the art. When the combination of the technical solutions is contradictory or cannot be realized, such a combination of the technical solutions should not be considered to exist, and is not within the protection scope of the present invention.

The present invention provides an aromatherapy diffuser, which is used to mount an essential oil bottle 40 to spray atomized essential oil.

In an embodiment of the present invention, as shown in FIGS. 1 to 7, the aromatherapy diffuser includes: a main body provided with a first mist hole 111;

an atomization component, wherein the essential oil bottle 40 is detachably mounted on the atomization component, and the atomization component is arranged in the main body; and a flow guiding member 30, wherein the flow guiding member 30 is arranged between a first mist hole 111 and the atomization component, the flow guiding member 30 includes a first flow guiding channel 31 and a second flow guiding channel 32 mutually communicated, the first flow guiding channel 31 is arranged in an arc shape, a horizontal section of an inner side wall of the first flow guiding channel 31 is higher than a liquid level in the essential oil bottle 40, one end of the first flow guiding channel 31 far away from the second flow guiding channel 32 is provided with a mist inlet 311 connected to the atomization component, and one end of the second flow guiding channel 32 far away from the first flow guiding channel 31 is provided with a mist outlet 321 connected to the first mist hole 111.

The aromatherapy diffuser is used to atomize and spray essential oil, and the main body is the main mounting structure of the aromatherapy diffuser, which is used to accommodate internal components and provide a mounting space.

The atomization component is used to atomize the essential oil, and the essential oil bottle 40 may be detachably mounted on the atomization component, so that a user replaces different types of essential oils or add essential oils. The atomization component generally includes an atomizer 22 and an air pump 23, and the air pump 23 provides an airflow, so that the essential oil is atomized by the atomizer 22 and sprayed via the flow guiding member 30.

The flow guiding member 30 is used to optimize the airflow path and prevent the essential oil from leaking. The first flow guiding channel 31 is designed in an arc shape, and a horizontal section of an inner side wall of the first flow guiding channel is higher than a liquid level in the essential oil bottle 40. It should be explained that the horizontal section of the inner side wall of the first flow guiding channel 31 refers to the horizontal section of the inner side wall at the highest point of the first flow guiding channel 31 when the aromatherapy diffuser is tilted in the transportation or use process. Due to the arc-shaped arrangement of the first flow guiding channel 31, the essential oil cannot directly flow into the second flow guiding channel 32 under the action of gravity, thereby preventing the essential oil from overflowing via the first mist hole 111, and achieving an anti-leakage function. The mist inlet 311 is communicated with the atomization component for guiding the atomized essential oil to enter the flow guiding member 30, and the mist outlet 321 is communicated with the first mist hole 111, so that the essential oil is atomized and then smoothly sprayed out, thereby improving the atomizing effect.

According to the technical solution of the present invention, the aromatherapy diffuser includes a main body, an atomization component arranged in the main body and a flow guiding member 30 connected to the atomization component and a first mist hole 111, wherein the atomization component is used to detachably mount an essential oil bottle 40 and atomize essential oil, the flow guiding member 30 includes a first flow guiding channel 31 and a second flow guiding channel 32 mutually communicated, the first flow guiding channel 31 is arranged in an arc shape, a horizontal section of an inner side wall of the first flow guiding channel is higher than a liquid level in the essential oil bottle 40, one end of the first flow guiding channel 31 far away from the second flow guiding channel 32 is provided with a mist inlet 311 connected to the atomization component, and one end of the second flow guiding channel 32 far away from the first flow guiding channel 31 is provided with a mist outlet 321 connected to the first mist hole 111. According to the foregoing structural design, when the aromatherapy diffuser is tilted, inverted or impacted, the arc-shaped arrangement of the first flow guiding channel 31 may ensure that the inner side wall of the flow guiding member 30 is always higher than the liquid level in the essential oil bottle 40, thereby preventing the essential oil from overflowing along the flow guiding member 30, and effectively preventing diffuser damage and environmental pollution caused by essential oil leakage. Therefore, the anti-leakage performance and the practicability of the aromatherapy diffuser are effectively improved.

Further, as shown in FIGS. 1 to 6, the first flow guiding channel 31 is arranged in an annular shape, and the mist outlet 321 is arranged close to a central axis of the flow guiding member 30 relative to the mist inlet 311. In this embodiment, the annular design of the first flow guiding channel 31 makes the boundary of the flow guiding member 30 more uniform, thereby ensuring that no matter from which direction or angle the aromatherapy diffuser is tilted, the inner wall of the flow guiding member 30 always remains higher than the liquid level in the essential oil bottle 40, preventing the essential oil in the aromatherapy diffuser from overflowing due to tilting, and further achieving the anti-leakage function.

In addition, the mist outlet 321 is arranged close to the central axis relative to the mist inlet 311, so that an included angle is formed between the first flow guiding channel 31 and the second flow guiding channel 32. This design further limits the leakage of the essential oil. In a case that the aromatherapy diffuser is tilted or inverted, the design of the included angle effectively prevents the essential oil from flowing into the second flow guiding channel 32, so that the essential oil is prevented from overflowing via the mist outlet 321. This structure optimizes the anti-leakage performance, and ensures the reliability of the aromatherapy diffuser and long-term stable use.

Further, the mist outlet 321 is positioned at a central position of the flow guiding member 30. In this embodiment, the mist outlet 321 is arranged at a central position of the flow guiding member 30, so as to optimize the spraying direction of the atomized essential oil; therefore, the atomized essential oil may be uniformly and stably sprayed from the central position. This design is beneficial to the uniform distribution of airflow after the essential oil is atomized, thereby improving the atomization effect and ensuring that the atomized essential oil of the aromatherapy diffuser may cover a wider area.

Further, the mist inlet 311 and the mist outlet 321 are arranged in opposite directions along an axial direction of the flow guiding member 30. It should be noted that axially opposite means that the opening directions of the mist inlet 311 and the mist outlet 321 are arranged toward the opposite sides of the first flow guiding channel 31 relative to the first flow guiding channel 31.

Figure 4:
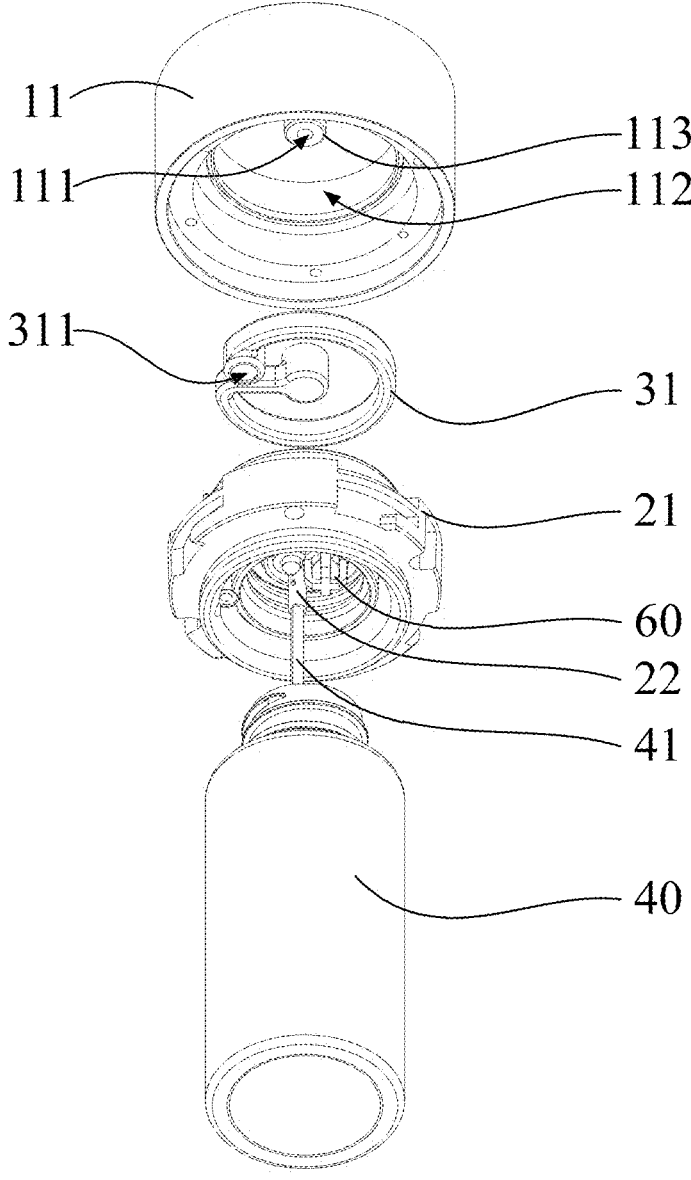
FIG. 4 is a schematic structural diagram of a cover body, a flow guiding member, an atomization component and an essential oil bottle in an exploded state.
Figure 5:
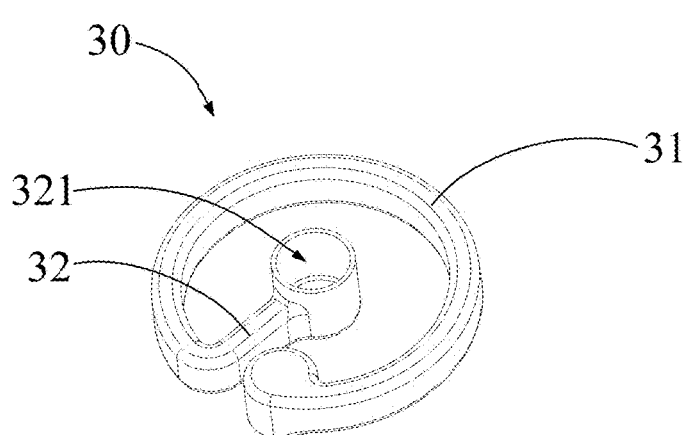
FIG. 5 is a schematic structural diagram of an embodiment of a flow guiding member at an angle.
Figure 6:
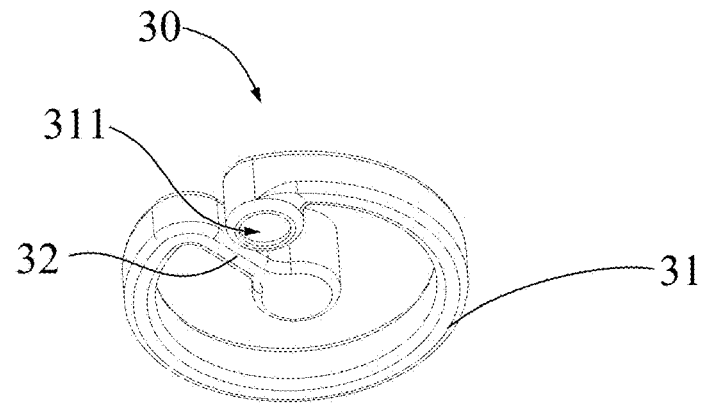
FIG. 6 is a schematic structural diagram of an embodiment of a flow guiding member at another angle.
Figure 7:
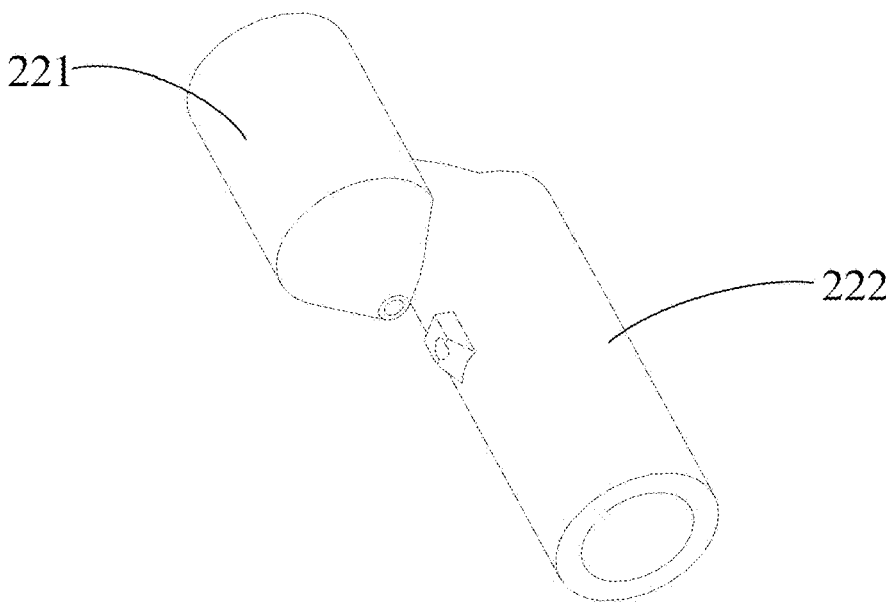
FIG. 7 is a schematic structural diagram of an atomizer at an angle.

Further, as shown in FIGS. 1 and 4, the first mist hole 111 is opened on a top surface of the main body. In this embodiment, the first mist hole 111 is positioned on the top surface of the main body, which can make the atomized essential oil spray upward evenly and stably, so that the environment around the main body may be purified, which effectively enhances the reliability and use effect of the aromatherapy diffuser and improves the user experience.

Further, as shown in FIGS. 1 to 4, the main body includes a mounting housing 12 and a cover body 11 detachably connected to the mounting housing 12, the atomization component is mounted on the cover body 11, the first mist hole 111 is opened at a top of the cover body 11, and the essential oil bottle 40 is positioned in the mounting housing 12. In this embodiment, the detachable connection design between the cover body 11 and the mounting housing 12 allows the user to easily disassemble and clean the internal components of the aromatherapy diffuser. Specifically, the atomization component is mounted on the cover body 11, so that the user conveniently replaces the essential oil bottle 40 and performs routine maintenance. Meanwhile, the first mist hole 111 is positioned at the top of the cover body 11, so that atomized essential oil may be smoothly sprayed out from the top, and blockage or obstruction of spraying is avoided. The essential oil bottle 40 is positioned in the mounting housing 12, which is helpful for stabilizing the storage and supply of the essential oil and ensuring the reliability and stability of the aromatherapy diffuser in the using process.

Further, as shown in FIGS. 1 to 6, the cover body 11 is provided with a rectifying cavity 112, the flow guiding member 30 is arranged in the rectifying cavity 112, and the atomization component and the mist inlet 311 are both communicated with the rectifying cavity 112. In this embodiment, the design of the rectifying cavity 112 can effectively balance and guide the airflow, and ensure that the atomized essential oil can smoothly enter the flow guiding member 30. The flow guiding member 30 is arranged in the rectifying cavity 112, so as to optimize the flow path of the essential oil airflow, reduce the disorderly disturbance in the airflow, and thus improve the atomization efficiency.

In addition, the communication design between the atomization component and the mist inlet 311 and the rectifying cavity 112 facilitates the smooth transition of the airflow, so that the atomized essential oil may evenly and stably enter the flow guiding member 30 and be sprayed out via the mist outlet 321, which effectively improves the atomization effect of the aromatherapy diffuser and enhances the stability and overall performance of the aromatherapy diffuser.

Further, as shown in FIGS. 1 to 5, a fixing column 113 protrudes from a peripheral side of the first mist hole 111 in the rectifying cavity 112, and the mist outlet 321 of the flow guiding member 30 is sleeved on the fixing column 113. In this embodiment, the fixing column 113 is used to fix the flow guiding member 30, so as to ensure that the mist outlet 321 is stably positioned in the rectifying cavity 112 and prevent the mist outlet from being displaced or loosened during use. The mist outlet 321 is sleeved on the fixing column 113 to ensure a stable spraying path of the essential oil airflow, thereby improving the atomization effect and the accuracy of essential oil spraying. The first mist hole 111 passes through the fixing column 113 and is connected to the flow guiding member 30.

Further, as shown in FIGS. 1 to 4, the atomization component includes a first mounting bracket 21, an atomizer 22 fixedly mounted on the first mounting bracket 21, and an air pump 23 arranged in the mounting housing 12, one end of the atomizer 22 is communicated with a liquid in the essential oil bottle 40 via a conduit 41, and another end of the atomizer is communicated with the air pump 23; the cover body 11 is provided with a mounting groove 114, the first mounting bracket 21 is fixedly arranged in the mounting groove 114, the rectifying cavity 112 is formed between the first mounting bracket 21 and an inner wall of the mounting groove 114, and the first mounting bracket 21 is provided with a second mist hole 211 communicated with the rectifying cavity 112 and the essential oil bottle 40. In this embodiment, the atomization component is stably mounted by the first mounting bracket 21, and the atomizer 22 is communicated with the liquid in the essential oil bottle 40 via the conduit 41, so as to ensure that the essential oil may be timely supplied to the atomizer 22 for atomization treatment. The air pump 23 provides airflow support for the atomizer 22 to promote atomization and spraying of the essential oil.

In addition, the design of the mounting groove 114 ensures that the first mounting bracket 21 may be securely mounted on the cover body 11, and a space between the first mounting bracket 21 and an inner wall of the mounting groove 114 forms the rectifying cavity 112. The rectifying cavity 112 may optimize the airflow path, reduce the disturbance in the airflow and improve the atomization efficiency. The design of the second mist hole 211 enables smooth connection between the rectifying cavity 112 and the essential oil bottle 40, and ensures that the essential oil may be effectively supplied to the atomizer 22 for atomization treatment.

Further, as shown in FIGS. 1 to 4 and FIG. 7, the atomization component further includes a second mounting bracket 24 arranged in the mounting housing 12, the second mounting bracket 24 is provided with an accommodating groove 241 for accommodating the essential oil bottle 40, the first mounting bracket 21 and the second mounting bracket 24 are mutually buckled to form a sealed cavity 25, the air pump 23 is arranged on the second mounting bracket and communicated with the sealed cavity 25, the first mounting bracket 21 is provided with an airflow channel 212, one end of the airflow channel 212 is communicated with the atomizer 22, and another end of the airflow channel is communicated with the sealed cavity 25. In this embodiment, the second mounting bracket 24 provides the accommodating groove 241 of the essential oil bottle 40, which effectively fixes the position of the essential oil bottle 40, and ensures that the essential oil bottle 40 does not displace in the using process. The first mounting bracket 21 and the second mounting bracket 24 are mutually buckled to form a sealed cavity 25. The design of the sealed cavity 25 may effectively isolate the outside air and the airflow path, thereby ensuring the stability of the airflow and the atomization effect of the essential oil in the atomization process.

The air pump 23 is arranged on the second mounting bracket 24 and communicated with the sealed cavity 25, and the airflow provided by the air pump 23 can support the atomizer 22 to atomize the essential oil. The airflow channel 212 formed in the first mounting bracket 21 is connected to the atomizer 22 via one end and is connected to the sealed cavity 25 via another end, which helps smooth airflow and ensures that the essential oil is atomized and sprayed out from the atomizer 22.

Specifically, the atomizer 22 includes a first channel 221 and a second channel 222, one end of the first channel 221 is communicated with the airflow channel 212, another end is opened toward the inside of the essential oil bottle 40 and close to one end of the second channel 222, another end of the second channel 222 is connected to the conduit 41 extending to the inside of the essential oil bottle 40, one end of the second channel 222 close to the first channel 221 is used to spray the liquid in the essential oil bottle 40, and the axis of the first channel 221 is perpendicular to the axis of the second channel 222.

When the aromatherapy diffuser is used, the air pump 23 pressurizes the sealed cavity 25, air enters the airflow channel 212 and then enters the essential oil bottle 40 via the first channel 221 of the atomizer 22, so that air pressure inside the essential oil bottle 40 is increased, essential oil liquid inside the essential oil bottle 40 is pressed into the conduit 41, then flows into the second channel 222 and is discharged from one end of the second channel 222 close to the first channel 221. Due to the fact that the first channel 221 and the second channel 222 are arranged oppositely and vertically, the air blown into the essential oil bottle 40 by the air pump 23 intersects with the essential oil liquid at the adjacent end of the first channel 221 and the second channel 222, the essential oil liquid is scattered and misted into essential oil mist by the air, the essential oil mist moves upwards, flows into the rectifying cavity 112 via the second mist hole 211 and flows through the flow guiding member 30, and then the essential oil mist is discharged via the first mist hole 111.

Further, as shown in FIGS. 1 to 4, a check valve 50 is also arranged in the airflow channel 212. In this embodiment, the check valve 50 is mounted in the airflow channel 212 to prevent the airflow from flowing in the reverse direction. When the air pump 23 works, the airflow in the airflow channel 212 is forced to push to be atomized by the atomizer 22, and the check valve 50 can prevent the airflow or essential oil from flowing back into the sealed cavity 25 to pollute the device, thereby improving the performance and the use stability of the aromatherapy diffuser.

Further, as shown in FIGS. 1 to 4, an anti-overflow ball valve 60 is arranged on one side of the second mist hole 211 facing the essential oil bottle 40. In this embodiment, the anti-overflow ball valve 60 is a valve with a spherical structure, which is mounted close to the second mist hole 211 and faces one side of the essential oil bottle 40. The function of the anti-overflow ball valve 60 is to prevent the essential oil from overflowing via the second mist hole 211 due to gravity when the aromatherapy diffuser is in a tilted or inverted state.

The spherical structure in the anti-overflow ball valve 60 may be freely adjusted according to the pressure change of the liquid, so that the essential oil is prevented from over-flowing under the action of external force. When the aro-matherapy diffuser is in a normal working state, the anti-overflow ball valve 60 is opened, so that the atomized essential oil is allowed to flow smoothly and is guided out by the flow guiding member 30 via the second mist hole 211; and when the aromatherapy diffuser inclination is tilted at an excessively large angle or inverted, the anti-overflow ball valve 60 automatically closes to prevent the essential oil from leaking, thereby ensuring that the interior of the aromatherapy diffuser remains clean and preventing the external environment from being contaminated by the essen-tial oil. Therefore, the practicality of the aromatherapy diffuser is improved.

Meanwhile, the flow guiding member 30 effectively ensures that the essential oil does not leak when the aroma-therapy diffuser is at any angle, thereby effectively improv-ing the practicality of the aromatherapy diffuser.

Further, as shown in FIGS. 1 to 4, the atomization component further includes a flow divider 27, and the flow divider 27 is arranged in the rectifying cavity 112 and corresponds to the second mist hole 211. In this embodi-ment, the function of the flow divider 27 is to divide the airflow path, thereby effectively distributing the atomized essential oil passing through the second mist hole 211, so that the atomized essential oil is more evenly distributed in the rectifying cavity 112, avoiding uneven or over-concen-trated airflow, thereby affecting the atomization effect of the aromatherapy diffuser. This design further improves the atomization efficiency and stability of the aromatherapy diffuser.

Figure 2:
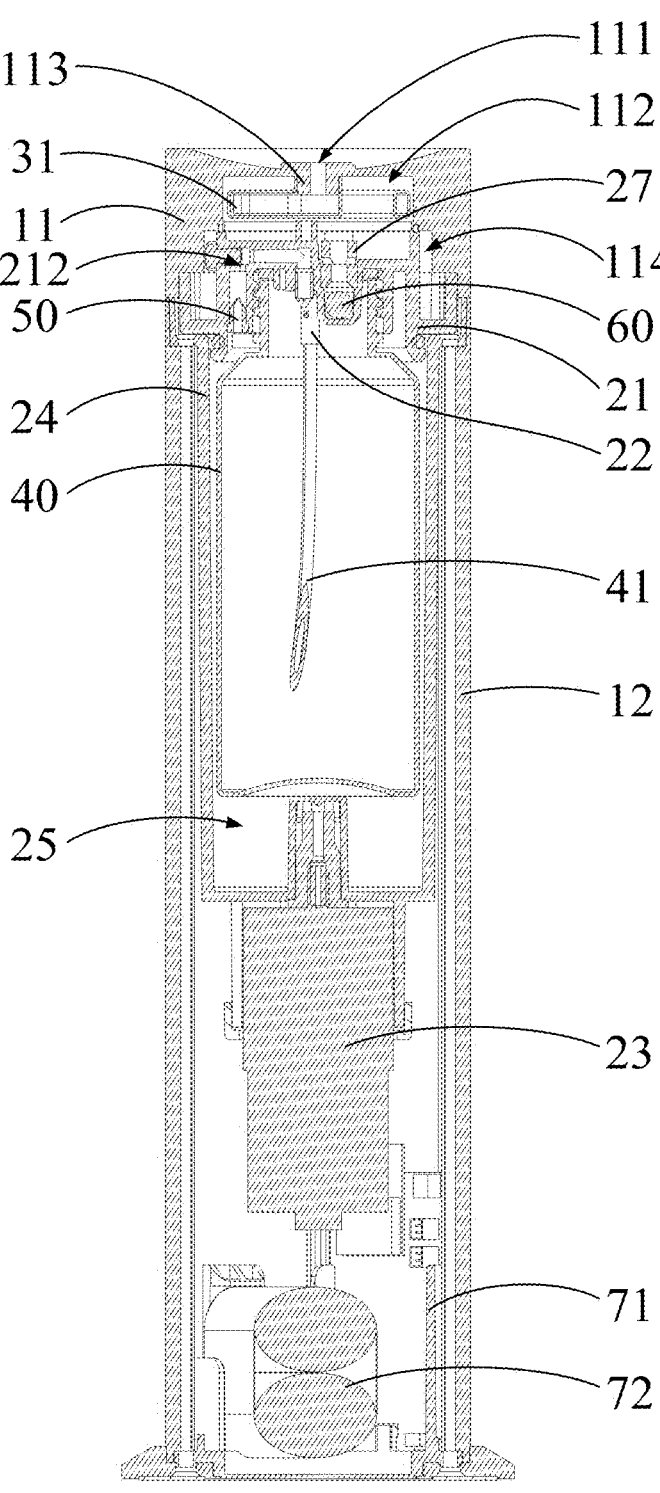
FIG. 2 is a schematic diagram of a cross-sectional structure of an aromatherapy diffuser according to an embodiment of the present invention.
Figure 3:
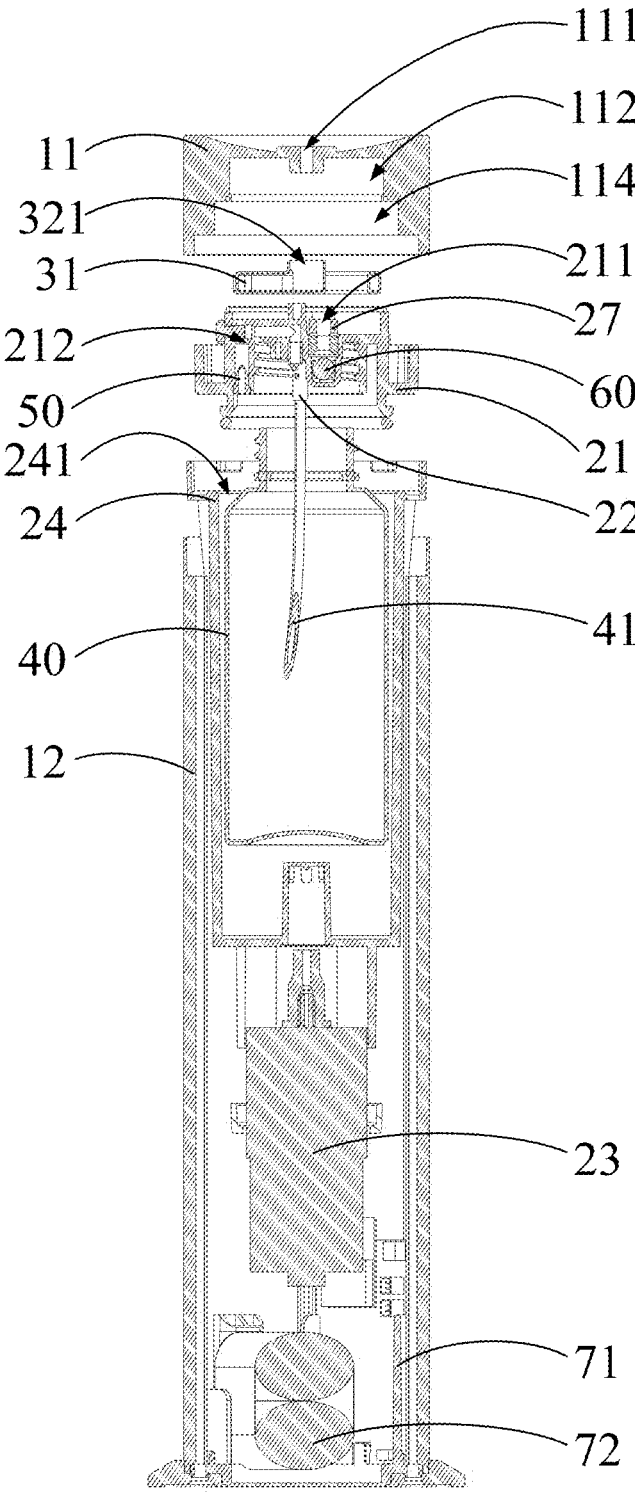
FIG. 3 is a schematic diagram of a cross-sectional structure of an aromatherapy diffuser according to the present invention in an exploded state.

Further, as shown in FIGS. 1 to 3, the aromatherapy diffuser further includes a control component, the control component includes a main control board 71 and a battery electrically 72 connected to the main control board 71, and the main control board 71 is electrically connected to the air pump 23. In this embodiment, the function of the control component is to intelligently control the working state of the aromatherapy diffuser to ensure that the aromatherapy dif-fuser can operate efficiently and stably. The main control board 71 is the core control component of the aromatherapy diffuser, which is powered by the battery 72 and is electri-cally connected to the air pump 23 to control the start and stop of the air pump 23 and working intensity of the air pump. When the user activates the aromatherapy diffuser, the main control board 71 controls the working state of the air pump 23 by receiving the user's operation instructions (such as turning on, turning off, adjusting the atomization intensity), thereby achieving the atomization effect of the essential oil.

The battery 72 is used to provide the required power for the entire system, ensuring the independent operation of the aromatherapy diffuser. With the electrical connection between the main control board 71 and the air pump 23, the working mode of the aromatherapy diffuser may be flexibly adjusted to enhance the user experience.

Further, as shown in FIGS. 1 to 6, the flow guiding member 30 is an integrally formed structure. In this embodi-ment, the flow guiding member 30 is designed to be inte-grally formed, so that the flow guiding member 30 is formed by integral mold processing during the production process, which avoids the splicing of a plurality of parts, thereby improving the overall stability and sealing of the structure. Specifically, the flow guiding member 30 may be manufac-tured as an integral structure by blow molding, or may be manufactured as an integral structure by ultrasonic welding. This is not limited herein.

Figure 8:
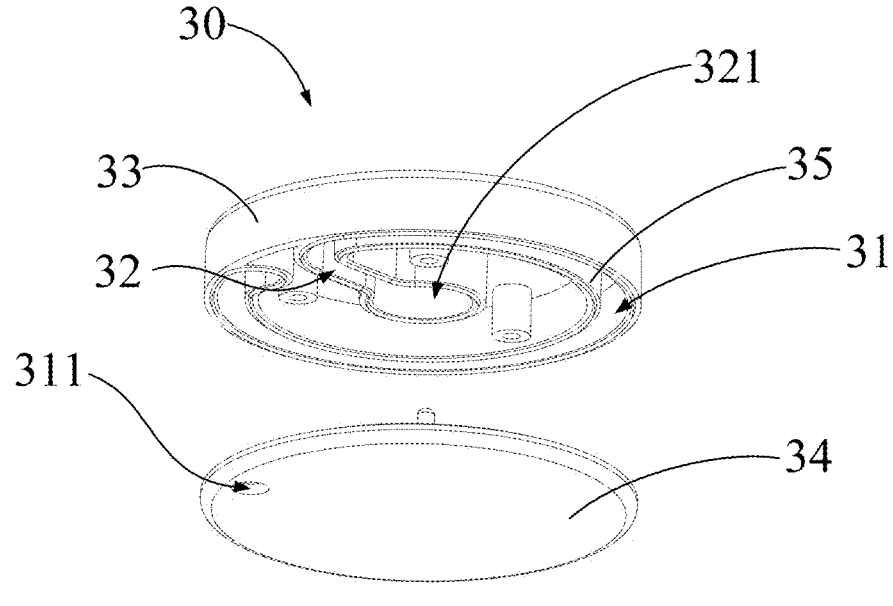
FIG. 8 is a schematic diagram of an exploded structure of another embodiment of a flow guiding member at an angle.
Figure 9:
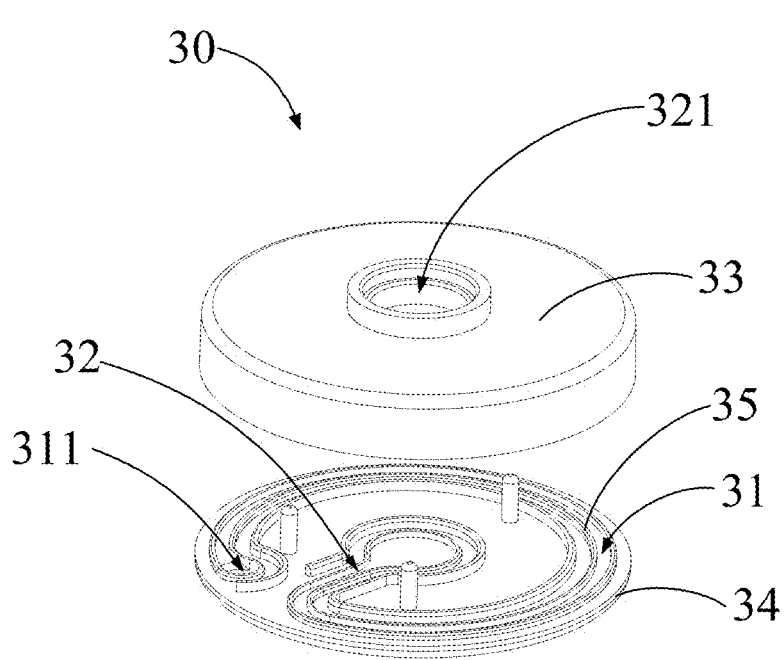
FIG. 9 is a schematic diagram of an exploded structure of another embodiment of a flow guiding member at another angle.

As shown in FIGS. 8 and 9, in another embodiment, the flow guiding member 30 may further include an upper housing 33 and a lower housing 34 mutually fastened, and a partition 35 for forming a flow guiding channel is arranged in the upper housing 33 and the lower housing 34, wherein the mist inlet 311 is opened in the lower housing 34, and the mist outlet 321 is opened in the upper housing 33.

The above mentioned contents are only optional embodi-ments of the present invention and are not intended to limit the patent scope of the present invention, and under the invention concept of the present invention, the equivalent structural transformations made by using the contents of the specification and the drawings of the present invention, or direct/indirect applications to other related technical fields, are all included in the patent protection scope of the present invention.

The invention claimed is:

1. A aromatherapy diffuser, used to mount an essential oil bottle to spray atomized essential oil, comprising:
   a main body provided with a first mist hole;
   an atomization component, wherein the essential oil bottle is detachably mounted on the atomization component, and the atomization component is arranged in the main body; and
   a flow guiding member, wherein the flow guiding member is arranged between the first mist hole and the atomization component, the flow guiding member comprises a first flow guiding channel and a second flow guiding channel mutually communicated, the first flow guiding channel is arranged in an arc shape, a horizontal section of an inner side wall of the first flow guiding channel is higher than a liquid level in the essential oil bottle, one end of the first flow guiding channel far away from the second flow guiding channel is provided with a mist inlet connected to the atomization component, and one end of the second flow guiding channel far away from the first flow guiding channel is provided with a mist outlet connected to the first mist hole;

wherein the first flow guiding channel is arranged in an annular shape, and the mist outlet is arranged close to a central axis of the flow guiding member relative to the mist inlet.

2. The aromatherapy diffuser according to claim 1, wherein the mist outlet is positioned at a central position of the flow guiding member.

3. The aromatherapy diffuser according to claim 2, wherein the mist inlet and the mist outlet are arranged in opposite directions along an axial direction of the flow guiding member.

4. The aromatherapy diffuser according to claim 3, wherein the first mist hole is opened on a top surface of the main body.

5. The aromatherapy diffuser according to claim 1, wherein the main body comprises a mounting housing and a cover body detachably connected to the mounting housing, the atomization component is mounted on the cover body, the first mist hole is opened at a top of the cover body, and the essential oil bottle is positioned in the mounting housing.

6. The aromatherapy diffuser according to claim 5, wherein the cover body is provided with a rectifying cavity, the flow guiding member is arranged in the rectifying cavity, and the atomization component and the mist inlet are both communicated with the rectifying cavity.

7. The aromatherapy diffuser according to claim 6, wherein a fixing column protrudes from a peripheral side of the first mist hole in the rectifying cavity, and the mist outlet of the flow guiding member is sleeved on the fixing column.

8. The aromatherapy diffuser according to claim 6, wherein the atomization component comprises a first mounting bracket, an atomizer fixedly mounted on the first mounting bracket, and an air pump arranged in the mounting housing, one end of the atomizer is communicated with a liquid in the essential oil bottle via a conduit, and another end of the atomizer is communicated with the air pump; and the cover body is provided with a mounting groove, the first mounting bracket is fixedly arranged in the mounting groove, the rectifying cavity is formed between the first mounting bracket and an inner wall of the mounting groove, and the first mounting bracket is provided with a second mist hole communicated with the rectifying cavity and the essential oil bottle.

9. The aromatherapy diffuser according to claim 8, wherein the atomization component further comprises a second mounting bracket arranged in the mounting housing, the second mounting bracket is provided with an accommodating groove for accommodating the essential oil bottle, the first mounting bracket and the second mounting bracket are mutually buckled to form a sealed cavity, the air pump is arranged on the second mounting bracket and communicated with the sealed cavity, the first mounting bracket is provided with an airflow channel, one end of the airflow channel is communicated with the atomizer, and another end of the airflow channel is communicated with the sealed cavity.

10. The aromatherapy diffuser according to claim 9, wherein a check valve is also arranged in the airflow channel.

11. The aromatherapy diffuser according to claim 8, wherein an anti-overflow ball valve is arranged on one side of the second mist hole facing the essential oil bottle.

12. The aromatherapy diffuser according to claim 8, wherein the atomization component further comprises a flow divider, and the flow divider is arranged in the rectifying cavity; the flow divider is configured to divide an airflow path and distribute the atomized essential oil passing through the second mist hole.

13. The aromatherapy diffuser according to claim 8, wherein the aromatherapy diffuser further comprises a control component, the control component comprises a main control board and a battery electrically connected to the main control board, and the main control board is electrically connected to the air pump.

14. The aromatherapy diffuser according to claim 1, wherein the flow guiding member is an integrally formed structure.

15. The aromatherapy diffuser according to claim 1, wherein the first flow guiding channel and the second flow guiding channel are in a plane substantially perpendicular to an axle of the essential oil bottle.

\* \* \* \* \*